US00PP14942P2

(12) United States Plant Patent
Olesen et al.

(10) Patent No.: US PP14,942 P2
(45) Date of Patent: Jun. 22, 2004

(54) MINIATURE ROSE PLANT 'POULGO006'

(50) Latin Name: *Rosa hybrida*
Varietal Denomination: POULgo006

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/264,509

(22) Filed: Oct. 4, 2002

(51) Int. Cl.[7] ..... A01H 5/00
(52) U.S. Cl. ..... Plt./121
(58) Field of Search ..... Plt./121

*Primary Examiner*—Bruce R. Campell
*Assistant Examiner*—June Hwu

(57) ABSTRACT

A new miniature rose which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Classification:

Botanical: *Rosa hybrida* 'POULgo006'.

Commercial: Miniature.

The present invention constitutes a new and distinct variety of hanging basket rose plant which originated from a controlled crossing between an unnamed, non-patented seedling and 'POULmanti', illustrated in U.S. Plant Pat. No. 11,540, issued on Oct. 3, 2000. The two parents were crossed and the resulting seeds were planted in a controlled environment. The new variety is named 'POULgo006'.

The new variety may be distinguished from its pollen parent, 'POULmanti', created by the same inventors, by the following combination of characteristics:

1. The general tonality of 'POULmanti' is Red Group 55B, while that of 'POULgo006' is Red-Purple Group 62C.
2. The petal count of 'POULmanti' is 40 to 50, while that of 'POULgo006' is 20 to 25.
3. 'POULmanti' has a growth habit which makes it suitable for garden use, while the habit of 'POULgo006' is appropriate for use in hanging baskets.

The new variety may be distinguished from its seed parent, unnamed, by the following combination of characteristics:

1. The general tonality of the unnamed seed parent is Red-Purple Group 65D while that of 'POULgo006' is Red-Purple Group 62C.
2. The diameter of the open flower of the unnamed seed parent is 60 to 65 mm while that of 'POULgo006' is 60 to 70 mm.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULgo006' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULgo006' was selected by the inventors as a single plant from the progeny of the hybridization in May of 2000.

Asexual reproduction of 'POULgo006' by cuttings and traditional budding was first done by L. Pernille and Mogens N. Olesen in their nursery in Fredensborg, Denmark in May of 2001. This initial and other subsequent propagations conducted in controlled environments have demonstrated that the characteristics of 'POULgo006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULgo006'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Bare stem exhibiting thorns;
6. Leaves.

DETAILED DESCRIPTION OF THE VARIETY

The following is a description of 'POULgo006', as observed in its growth in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULgo004', a rose variety from the same inventors described and illustrated in U.S. Plant Pat. No. 13,592, dated Feb. 25, 2003, are compared to 'POULgo006' in Chart 1.

CHART 1

| | 'POULgo006' | 'POULgo004' |
|---|---|---|
| Petal Count. | 20 to 25. | 85 to 90. |
| Petal color, upper surface. | Red-Purple Group 62B. | Red Group 53C. |
| Petal color, lower surface. | Red-Purple Group 58C. | Red Group 53B. |

Parents: An unnamed seedling×'POULmanti'

FLOWER AND FLOWER BUD

Blooming habit: Continuous.

Flower bud:

*Size.*—Upon opening, 20 to 25 mm in length from base of receptacle to end of bud.

*Bud form.*—Pointed ovoid.

*Bud color.*—As sepals unfold, Red-Purple Group 58B and C; At ¼ opening, Red-Purple Group 62A.

*Sepals.*—Upper surface: Yellow-Green Group 146B. Lower surface: Yellow-Green Group 146B. Surfaces are moderately pubescent. Shape: Sepal apex is cirrose. Base is flat at union with peduncle. Size: 21 mm long×10 mm wide.

*Receptacle.*—Surface: Smooth. Shape: Funnel shaped. Size: 5 mm (h)×6 mm (w). Color: Green Group 143B.

*Peduncle.*—Surface: With many stipitate glands. Length: 35 to 40 mm average length. Color: Yellow-Green Group 146C. Strength: Weak.

*Borne.*—5 to 7 buds per stem.

*Anthocyanin.*—Greyed-Red Group 181A.

Flower bloom:

*Fragrance.*—Light.

*Duration.*—As a pot plant, flowers last from 10 to 12 days. Petals fall cleanly away from plant.

*Size.*—Medium. Average flower diameter is 60 to 70 mm when open.

*Form.*—Shape of flower when viewed from the side: Upon opening, upper part: Flat. Upon opening, lower part: Flat. Open flower, upper part: Flattened convex. Open flower, lower part: Concave.

*Petalage.*—Average range: Double. 20 to 25 petals under normal conditions with 3 to 5 petaloids.

Color:

*Upon opening, petals.*—Outermost petals: Outer Side: Red-Purple Group 58C. Inner Side: Red-Purple Group 62C. Innermost petals: Outer Side: Red-Purple Group 58C. Inner Side: Red-Purple Group 62A.

*Upon opening, basal petal spots.*—Outermost petals: Outer Side: Green-Yellow Group 1B. Inner Side: Green-Yellow Group 1C. Innermost petals: Outer Side: Green-Yellow Group 1A. Inner Side: Green-Yellow Group 1B.

*After opening, petals.*—Outermost petals: Outer Side: Red-Purple Group 62B and C. Inner Side: Red-Purple Group 62D. Innermost petals: Outer Side: Red-Purple Group 62B and C. Inner Side: Red-Purple Group 62D.

*After opening, basal petal spots.*—Outermost petals: Outer Side: Yellow-Green Group 150D. Inner Side: Yellow-Green Group 150D. Innermost petals: Outer Side: Yellow-Green Group 150D. Inner Side: Yellow-Green Group 150D.

General Tonality: On open flower Red-Purple Group 62B. No change in the general tonality at the end of the 5$^{th}$ day. Afterwards, general tonality is Red-Purple Group 62C.

Petals:

*Petal reflex.*—Strong.

*Petal edge.*—Ruffled, with notch in center.

*Shape.*—General shape is obcordate. The apex is round and the base is round.

*Size.*—25 mm long by 25 mm wide.

*Texture.*—Smooth.

*Petaloids.*—Quantity: 3 to 5. Size: 8 mm long and 5 mm wide. Color: Red-Purple Group 62D and Red-Purple Group 62B.

*Thickness.*—Thin.

*Arrangement.*—Not formal.

Reproductive organs:

*Pistils.*—Length: 9 to 10 mm long. Quantity: 60.

*Pollen.*—Quantity: None observed.

*Anthers.*—Size: 1 to 2 mm long. Color: Yellow-Orange Group 22A. Quantity: 100.

*Filaments.*—Color: Yellow-Green Group 150B. Length: 5 mm.

*Stigmas.*—Slightly inferior in location to anthers. Color: Green-Yellow Group 1C.

*Styles.*—Color: Yellow-Green Group 150C.

PLANT

Plant growth: Low and spreading. When grown as a nursery plant on its own roots the average plant height is 32 cm and the average plant width is 65 to 70 cm.

Stems:

*Color.*—Young wood: Yellow-Green Group 146C. Older wood: Yellow-Green Group 146B.

*Prickles.*—Incidence: 14 to 16 thorns per 10 cm of stem. Size: Average length: 6 to 7 mm. Color: Greyed-Yellow Group 160A. Shape: Deeply concave.

*Surface.*—Young wood: Smooth. Older wood: Rough.

Plant foliage: Normal number of leaflets on leaves in middle of the stem: 5 leaflets.

*Leaf size.*—80 to 85 mm (1)×60 to 65 mm (w).

*Quantity.*—Average.

*Color.*—Upper Leaf Surface: Green Group 137A. Lower Leaf Surface: Yellow-Green Group 146B. Juvenile foliage: Upper Leaf Surface: Green Group 137A. Lower Leaf Surface: Yellow-Green Group 146C. Anthocyanin intonation: Location: On lower surfaces of leaflets. Color: Greyed-Red Group 178A.

Plant leaves and leaflets:

*Stipules.*—Size: 12 to 15 mm long. Color: Margins are Yellow-Green Group 146A and C. Interior is Yellow-Green Group 145A. Stipitate glands: On leaflet margins. Anthocyanin: Scant. Greyed-Red group 181A.

*Petiole.*—Length: 4 to 8 mm long. Color: Yellow-Green Group 146B. Underneath: With occasional small thorn. Margins: With sparse stipitate glands.

*Rachis.*—Color: Yellow-Green Group 146B. Underneath: With occasional small thorn. Margins: With sparse stipitate glands.

*Leaflet.*—Edge: Finely serrated. Shape: Ovate. Apex shape is cuspidate. Base shape is rounded. Glossiness: Moderate. Texture: Leathery. Arrangement: Odd pinnate. Venation: Reticulate.

Disease resistance:

Average resistance to mildew, black spot, and Botrytis under normal growing conditions in Jackson County, Oreg.

Cold hardiness:

'POULgo006' has been found cold tolerant to USDA cold hardiness zone 6.

What is claimed is:

1. A new and distinct variety of rose plant of the miniature class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the horticultural industry.

* * * * *

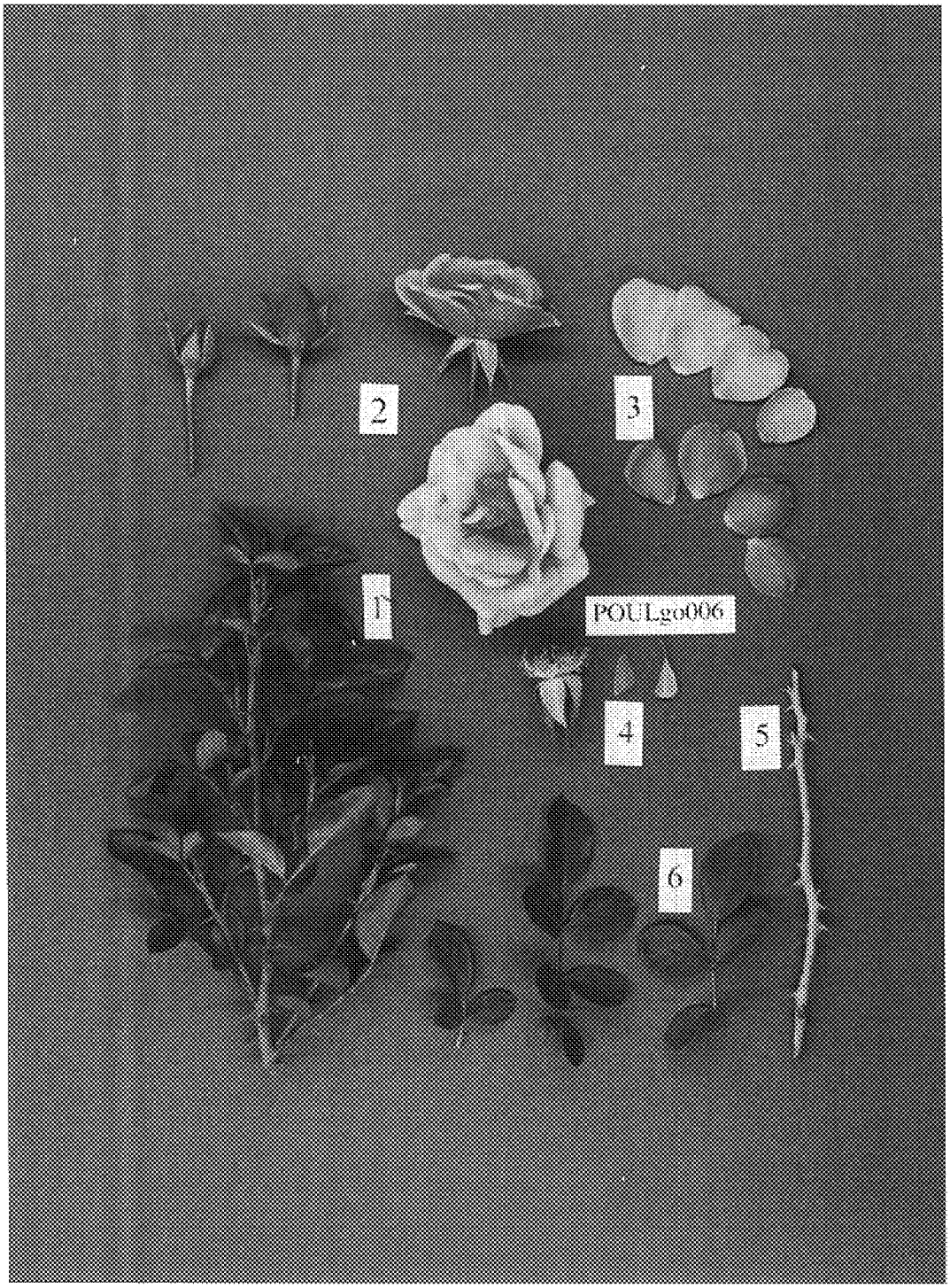
2
3
1
POULgo006
4
5
6